United States Patent
Hoffmann et al.

(10) Patent No.: US 12,286,676 B2
(45) Date of Patent: Apr. 29, 2025

(54) METHOD FOR COUNTING CELL TYPES OR CELL MARKERS IN A SAMPLE, IN PARTICULAR IN A BLOOD SAMPLE

(71) Applicant: Robert Bosch GmbH, Stuttgart (DE)

(72) Inventors: Jochen Hoffmann, Renningen (DE); Tino Frank, Lucerne (CH)

(73) Assignee: Robert Bosch GmbH, Stuttgart (DE)

( * ) Notice: Subject to any disclaimer, the term of this patent is extended or adjusted under 35 U.S.C. 154(b) by 862 days.

(21) Appl. No.: 17/423,344

(22) PCT Filed: Feb. 27, 2020

(86) PCT No.: PCT/EP2020/055143
§ 371 (c)(1),
(2) Date: Jul. 15, 2021

(87) PCT Pub. No.: WO2020/178134
PCT Pub. Date: Sep. 10, 2020

(65) Prior Publication Data
US 2022/0081717 A1  Mar. 17, 2022

(30) Foreign Application Priority Data
Mar. 1, 2019  (DE) ..................... 10 2019 202 788.1

(51) Int. Cl.
*C12Q 1/6883* (2018.01)
*C12N 15/10* (2006.01)
*C12Q 1/6806* (2018.01)
*C12Q 1/6844* (2018.01)

(52) U.S. Cl.
CPC ....... *C12Q 1/6883* (2013.01); *C12N 15/1003* (2013.01); *C12Q 1/6806* (2013.01); *C12Q 1/6844* (2013.01)

(58) Field of Classification Search
CPC .. C12Q 1/6883; C12Q 1/6806; C12Q 1/6844; C12Q 2600/158; C12Q 1/6886; C12N 15/1003
See application file for complete search history.

(56) References Cited

U.S. PATENT DOCUMENTS

| 2006/0286558 A1 | 12/2006 | Novoradovskaya et al. |
| 2018/0252722 A1 | 9/2018 | Wang |

FOREIGN PATENT DOCUMENTS

| CN | 106282116 A | 1/2017 |
| DE | 196 07 202 A1 | 8/1997 |
| JP | 2016-186454 A | 10/2016 |
| WO | 2007/147018 A1 | 12/2007 |
| WO | 2008/127356 A2 | 10/2008 |
| WO | 2014/133467 A1 | 9/2014 |
| WO | 2018/167312 A1 | 9/2018 |

OTHER PUBLICATIONS

Andergassen et al. Real-time RT-PCR systems for CTC detection from blood samples of breast cancer and gynaecological tumour patients (Review). 2016. Oncology Reports. 35: 1905-1915. (Year: 2016).*
Farrell Jr. RNA Methodologies: Laboratory guide for isolation and characterization. 2010. 4th Edition, Elsevier Acadmeic Press, Amsterdam, Chapter 2. (Year: 2010).*
Nel et al. Individual profiling of circulating tumor cell composition in patients with non-small cell lung cancer receiving platinum based treatmentTransl Lung Cancer Res, 2014, 3(2): 100-106. (Year: 2014).*
George-Gay et al. Understanding the complete blood count with differential. J Perianesth Nurs, 2003, 18: 96-114 (Year: 2003).*
International Search Report corresponding to PCT Application No. PCT/EP2020/055143, mailed Apr. 8, 2020 (German and English language document) (7 pages).
Leslie P. Silva et al., Measurement of DNA concentration as a normalization strategy for metabolomic data from adherent cell lines, Analytical Chemistry, Oct. 15, 2013, pp. 9536-9542, vol. 85.

* cited by examiner

*Primary Examiner* — Anand U Desai
*Assistant Examiner* — Amber K Faust
(74) *Attorney, Agent, or Firm* — Maginot, Moore & Beck LLP

(57) ABSTRACT

A method for detecting characteristic cells in a sample includes performing a first lysis of a sample to yield a first lysate wherein nuclei of the cells of the sample remain intact. Freely available RNA in the first lysate is extracted and classified to ascertain the amounts of various types of RNA in the first lysate. A second lysis operation on the previously lysed sample is performed to yield a second lysate wherein the cell nuclei of the cells in the sample are destroyed. DNA freely available in the second lysate is extracted and a total cell count of cells in the provided sample is calculated on the basis of the amount of extracted DNA. The number of cells having individual cell markers in the provided sample is calculated using the ascertained amounts of various types of RNA and the calculated total cell count.

11 Claims, 2 Drawing Sheets

METHOD FOR COUNTING CELL TYPES OR CELL MARKERS IN A SAMPLE, IN PARTICULAR IN A BLOOD SAMPLE

This application is a 35 U.S.C. § 371 National Stage Application of PCT/EP2020/055143, filed on Feb. 27, 2020, which claims the benefit of priority to Serial No. DE 10 2019 202 788.1, filed on Mar. 1, 2019 in Germany, the disclosures of which are incorporated herein by reference in their entirety.

BACKGROUND

The extraction or isolation of circulating tumor cells (CTCs) from blood is an important step in the analysis of blood for diagnosing tumor cells. Cells which are cytokeratin-positive, are CD45-negative, have a nucleus (DAPI detection) and are of epithelial origin are defined as CTCs. This definition is a guideline and is largely accepted in the liquid biopsy community. It is cells having these properties that are to be extracted or isolated.

Keratin (from Greek κέρας, kéras, "horn"; kératos in the genitive) is a collective term for various water-insoluble fibrous proteins which are formed by animals and characterize horny matter and assume mechanical functions in cells.

In line with their molecular structure as α-helix or β-sheet, a distinction is made between α- and β-keratins. Keratins are the main constituent of mammalian hair, fingernails and toenails, etc. α-Keratins (or cytokeratins) are present in the form of loosely organized keratin filaments. Cytokeratins (CKs or, in accordance with more recent nomenclature, also simply called keratins) are intermediate filaments which form proteins that provide mechanical support and perform a multiplicity of additional functions in cells. They are part of the cytoskeleton and the largest family of the intermediate filament proteins. A distinction is made between two types of cytokeratins, which form heterodimers, namely acidic type I (cytokeratins 9-23) and basic type II (cytokeratins 1-8).

Cytokeratins are typical markers in diagnostic pathology, especially for the detection of tumors. Primary tumors and metastases of a given carcinoma share the same pattern of cytokeratins that distinguishes them from other carcinoma types, thereby making it possible to distinguish between the various tumors.

CD45 is an antigen which can be used especially for detection of leukocytes (white blood cells).

Antigens are substances to which antibodies and certain lymphocyte receptors can specifically bind (it also being possible for the latter to bring about production of antibodies against the antigen). Antigens are usually proteins, but can also be carbohydrates, lipids or other substances. They can be recognized or bound by B-cell receptors or T-cell receptors or by antibodies (produced by B cells).

A cell is of epithelial origin when it originates from epithelial tissue. Epithelial tissue is a specific tissue type that is used as a collective name for covering tissue and glandular tissue. Epithelial tissue are cell layers which are single-layer or multilayer and which cover all inner and outer body surfaces of multicellular organisms. An exception here are joint capsules and bursae of the locomotor system. Epithelial tissue is, alongside muscle tissue, nervous tissue and connective tissue, one of the four basic tissue types in multicellular organisms.

A nucleus (DAPI detection) is proof that these cells have a cell nucleus—i.e., are not cells lacking a cell nucleus, such as, for example, red blood cells. Cells lacking a cell nucleus are fundamentally not considered to be CTCs, even if they meet the other stated criteria. The term "lysing" means that the cells or the cell membranes of the cells that are present in a cell suspension are destroyed, with the result that the individual constituents of the cells of the cell suspension are freely available in a solution. This facilitates later analysis.

The purpose of counting CTCs is to be able to establish in medical studies a clear link between overall survival (OS) and the post-therapeutically measured CTC counts. This means that pure counting of CTCs can already provide important information about OS or the effectiveness of a therapy. In order to obtain a more comprehensive picture of tumor status, CTC research is currently also focusing on the identification of genetic features from CTCs. Systems for automatic sorting, counting and classification of CTCs are therefore highly relevant.

For a genetic analysis of CTCs, it absolutely must be ensured that cells were actually also present in the sample. Otherwise, if no signals are present (=genetic feature not present), it is unclear whether no CTCs or generally no cells were in the sample, for example because the sample was contaminated and the detection reaction therefore did not generate signals.

What is therefore desirable is a method in which the absolute cell count of a sample can be counted.

One possibility is the counting of cells by means of performance of staining steps and automated processing of samples. However, such methods are realizable only with difficulty in fully automated workflows for clinical use—firstly, because image processing is usually necessary in order to analyze samples optically when certain stained features are identifiable—secondly, because staining steps frequently take longer. This too makes the clinical application of such methods difficult.

SUMMARY

What shall be described here is a method for the detection (or even the counting) of isolated CTCs by means of identification of genetic features. The method may also make it possible to dispense with staining steps.

The method serves for the detection of certain characteristic cells in a sample and comprises the following steps:
 a) providing a sample of cell suspension
 b) performing a first lysis operation with the sample to yield a first lysate of the sample, wherein the lysis is done in such a way that the cell nucleus of the cells of the cell suspension remains intact;
 c) extracting the ribonucleic acids (RNA) freely available in the first lysate;
 d) classifying the extracted ribonucleic acids in order to ascertain the amounts of various types of ribonucleic acids in the lysate of the sample;
 e) performing a second lysis operation with the remaining sample to yield a second lysate of the sample, wherein the lysis is done in such a way that cell nuclei of cells in the sample are destroyed,
 f) extracting the deoxyribonucleic acids (DNA) freely available in the second lysate,
 g) calculating a total cell count of cells in the sample on the basis of the amount of deoxyribonucleic acids
 h) calculating numbers having individual cell markers in the sample on the basis of the amounts of various types of ribonucleic acids as ascertained in step d) and the total cell count as calculated in step g).

The method is particularly preferred when the cell markers in step h) serve for identifying CTCs (circulating tumor cells).

The method is furthermore particularly preferred when the cell markers in step h) comprise at least one of the following markers:
- epithelial marker;
- EpCAM;
- CD45; and
- cytokeratin.

With said method, isolated CTCs are quantified without the need for a staining step for quantification. Here, the term "quantifying" means that the number of CTSs can be determined in absolute terms. The approach also allows the normalization of the sample, i.e., the establishment of how many cells are in the sample altogether in order to make the sample and the counted CTCs comparable with, respectively, other samples and CTCs counted in other samples.

The method is suitable for realization in a lab-on-α-chip-based fully automated workflow for point-of-care.

Step a) can, for example, comprise providing cells on a lab-on-a-chip system. Steps b) and e) are customary lysis operations which serve to break up membranes of cells and by means of which the constituents of the cells become identifiable. Extraction step c) serves for preparation for the subsequent analysis step d), and extraction step f) serves for preparation for the subsequent analysis steps g) and h).

A useful size of a sample for step a) comprises, for example, an amount of blood between 10 µl and 10 ml. Such a sample contains between $5 \times 10^7$ and $5 \times 10^{10}$ cells.

The core of this disclosure are methods for a quantitative detection of isolated CTCs via a multiparameter measurement of genetic features. This is done in step h), where the numbers of individual cell types are calculated. What is taken advantage of here is that the features determined via staining methods in the prior art (e.g., epithelial marker, EpCAM, CD45, cytokeratin) are also detectable in the cells are detectable on the basis of corresponding molecules, namely RNA (ribonucleic acids), especially mRNA (messenger RNA). This means that the cells react to certain dyes. When using staining methods, the existence of these molecules is thus indirectly already relied on in order to achieve classification of cells. With the described method, it is possible in a way to directly infer these molecules. Therefore, these molecules are ascertained, or classified, in step d) in order to determine amounts of various types of RNA. In the classification in step d), genetic detection is preferably used in order to achieve a classification of RNA under a certain feature (epithelial marker, EpCAM, CD45, cytokeratin).

How such genetic detection works in principle is that, when detecting RNA, reverse transcriptase (RT) is initially done from RNA (cDNA) so that this cDNA can be multiplied by means of a polymerase chain reaction (PCR), with quantification also taking place at the same time. All this together is then referred to as RT-PCR. DNA is detected simply by means of PCR (if detection is quantitative, then this is called qPCR). Various types of ribonucleic acids which are classified in step d) in order to determine the amounts thereof in the sample are especially ribonucleic acids which are markers for certain cancer cells. Firstly, the amounts of RNA (especially amounts of mRNA) of (surface) markers (e.g., epithelial marker, EpCAM, CD45, cytokeratin) mentioned above are preferably determined by means of PCR-based methods in step d). Here, EpCAM is considered to be a marker for cells of epithelial origin, and hence for cells originating from a tissue structure, i.e., CTCs; CD45 is a marker for white blood cells, i.e., for nonspecifically isolated cells; cytokeratins are proteins which are present in the cell interior of cells of epithelial origin, i.e., again a marker for CTCs. PCR (especially rtPCR=quantitative real-time PCR, or else qPCR) is a multiplication method for nucleic acids. Said multiplication method is based on the principle of the conventional polymerase chain reaction (PCR). In the PCR, quantification is carried out by means of fluorescence measurements, which are captured in real-time during a PCR cycle.

In addition, the total amount of isolated cells is determined via DNA. This is done by means of steps e), f) and g). Finally, the amounts determined at the mRNA level are related to the total amount of cells (step h).

The various steps of the described method can be varied in terms of their order. This especially applies to steps which do not directly build on one another and the order of processing of which can therefore be adapted. For example, step d) need not necessarily be done before e). The first lysate can also be temporarily stored, for example after the reverse-transcriptase step, and then analyzed simultaneously with the DNA detection of the second lysis. Steps c) and f) in particular can take place in parallel.

The method can also be referred to as a genetic counting method, the designation "counting method" referring here especially to step d).

The method has a multitude of advantages compared to known methods for detecting characteristic cells in a sample.

The main advantage of the method is that the number or quantitative ranges of tumor cells present in an isolated sample are measured on the basis of the measurement of genetic features. Thus, quantification of the amount of sample does not have to take place in an additional step. Quantification of the sample is necessary in order to be able to relate the measurement on the sample to other data and to thus give the sample informative value.

The method is in principle also suitable for detecting cancer-specific mutations, deletions or insertions on the basis of CTCs—by means of PCR-based methods in many cases. The method offers namely the advantage that such detections and the method presented here are, from the process steps, identical in principle, and are therefore particularly highly suited to cointegration on a lab-on-α-chip, since, here too, the quantity of the available amount of sample is an important basis of the design.

Staining methods have the fundamental disadvantage that it is difficult to draw clear conclusions from the images, which are evaluated electronically. For this purpose, a very high level of intelligence for image evaluation is required. In addition, there are no uniform standards for the determination of CTCs. The CANCER-ID consortium has developed the so-called ACCEPT5, which is intended to define a kind of standard for image evaluation. Measurement via the method described here (promises)/delivers more informative and clearer signals. In particular, a (classic) numerical evaluation can be done in step h). Moreover, the numerical evaluation done in step h) can include preparing a hemogram during a liquid biopsy.

The method according to the disclosure also promises easily detectable signals in the case of cells present in only small amounts in a sample, since a multiplicity of mRNA molecules are present in a cell in the case of transcribed active genes in the majority of cases. Said method thus relies on a marker, which is advantageous as regards amounts available, and said marker is especially advantageous over markers based on cellular DNA, of which there is fundamentally very much less available per cell.

These mRNA markers are combined with information at the DNA level, as a reliable source for the measurement of the total amount of cells in a sample. This has the advantage that the relative ratios determined at the mRNA level can be transformed/converted into absolute values by reference to DNA measurements. Clear normalization of the sample material occurs.

The described method can also achieve a reduction in manual steps in sample analysis. Depending on the isolation system, staining requires a multiplicity of process steps. Said process steps are unnecessary through the described method. The method proposed here allows simple automation and therefore saves costs and time.

The staining methods used in the prior art work with antibodies which also always bind nonspecifically. In the case of said methods, it is thus possible that undesired staining arises which distorts the result of subsequent counting of stained cells. Here, genetic detection delivers higher specificity. In addition, antibodies can exhibit variation during production and they vary in sensitivity or specificity depending on the manufacturing lot.

The method presented here allows an individual compilation of targets for which a sample is to be tested. This can be done by appropriately adapting the classification in step d) and the calculation/evaluation in step h). This universal method therefore allows application-specific use. Here, the term "target" means certain cell markers, for the existence of which the cell is to be tested or for which it is to be established how often they occur in the cells of the sample.

The method is not limited to applications in oncology. In general, said method offers a simplified process approach for analysis of expression patterns of cells for diagnostics. The method is advantageously usable especially in fully automated point-of-care applications.

In order to make the calculation/evaluation carried out by the method more precise, variation in the cell sizes of the cells in the sample is preferably taken into account at least in one of the two steps g) and h). This variation in the cell sizes can, for example, be established by an optical analysis (image analysis) of the sample or be obtained from statistical data. In variants of the method, the variation is permanently stored as a parameter for the calculation evaluation in steps g) and h).

The term "calculating" in steps g) and h) is not to be understood as meaning in a that the result yielded in step g) is necessarily an exact total cell count which definitively or actually corresponds to the precise number of cells in the sample. Nor is it meant here that, in step h), exactly calculate what numbers of cells having individual cell markers are definitively or actually contained in the sample. Because of uncertainties or stochastic inaccuracies in the input variables described for the calculations (amount of deoxyribonucleic acids for step g) and amounts of various types of ribonucleic acids for step h)), this may not even be possible at all. Instead, what is meant here by the step term "calculating" is that the ascertainment of the total number of cells or the ascertainment of the numbers of cells having individual cell markers is ascertained on the basis of the available input variables according to a mathematical rule and preferably no further estimated values or assumptions are taken as a basis therefor.

Particularly preferably, the variation in the cell sizes is determined via a housekeeping gene of the cells. With the aid of a housekeeping gene, estimations of the cell sizes are possible and size differences between the cells can thus be normalized and made comparable. Housekeeping genes are typically genes which encode the structural molecules and enzymes associated with the basal metabolism of cells, for example with glucose metabolism. On the basis of such genes, it is possible to infer a cell size.

The method is, moreover, particularly advantageous when the following step is performed before step h):

g2) distinguishing active ribonucleic acids and inactive ribonucleic acids. This yields further improved possibilities in evaluation for method steps h) and g).

Particularly, the estimation in step g) is done by a comparison of the amounts ascertained in step d) with a data matrix in which data concerning ribonucleic acids present are stored for each cell marker. Such a data matrix can be constructed depending on the nature of an expert system.

The method is particularly advantageous when the following step is performed before step c):

b2) extracting cytoplasm.

This additional step simplifies the later method steps. Moreover, said step make it possible to avoid errors in steps d), g) and h) that might be caused by the cytoplasm.

The method is additionally advantageous when the ribonucleic acids are converted into deoxyribonucleic acids for ascertainment of the amounts in step d). This conversion offers advantageous possibilities for classification.

It is further advantageous when the lysis in step b) is achieved by a change in an osmotic equilibrium in the sample, thereby bringing about bursting of the cell membranes of the cells. In this connection, it is especially advantageous when an osmotic equilibrium is set in step b) such that cell nuclei of cells in the sample remain intact. Such designing of the lysis operations can ensure that RNA and DNA do not mix for analysis steps d), g) and h).

BRIEF DESCRIPTION OF THE DRAWINGS

In what follows, the method is elucidated on the basis of the figures. The figures show a preferred exemplary embodiment to which the method, however, cannot be reduced. In the figures.

DETAILED DESCRIPTION

Figure 1:
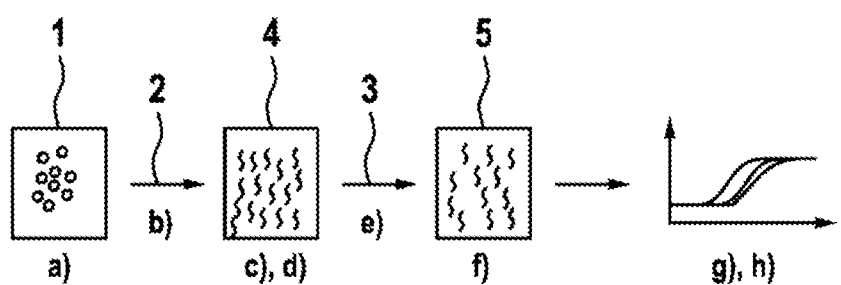
FIG. 1: shows a flow chart of the described method.

FIG. 1 depicts the applied process steps of the method in highly schematic form. Here, a (usually) preprocessed cell suspension 1 is lysed. Said cell suspension can be whole blood, serum, a cell purification product, or a sample sorted on a flow cytometer. As an alternative to a cell suspension, it is also possible to use cells adherent to a surface for the method. In particular, it is possible to use cells which adhere to a biopsy needle functionalized for the method.

The first lysis operation 2 (step b)) is depicted here by an arrow. The first lysis operation 2 generates a first lysate 4, which can be analyzed with steps c) and d).

In the case of a typical amount of a starting sample of 1 ml [milliliter], step b) preferably yields an amount of 2 ml to 4 ml of first lysate.

The second lysis operation 3 (step e)) is likewise depicted here by an arrow. The second lysis operation 3 generates a second lysate 5, which can be analyzed with steps f), g) and h).

In the case of a typical amount of a starting sample of 2 ml [milliliter] to 4 ml, step e) preferably yields an amount of 4 ml to 8 ml of a second lysate.

The lysis mode used in step b) (first lysis operation) can be chosen as desired, but must be compatible with the subsequent RT-qPCR. In particular, purification of the lysate must be dispensed with, since material to be quantified may otherwise be lost. A suitable lysis method can be achieved via the immobilization of the cellular material in a cannula. A lysis buffer can then be drawn into the cannula in order to extract nucleic acids such as DNA or RNA from the cellular material. This involves first drawing in a hypotonic solution (the lysis buffer), the salt content of the buffer being higher than that of the cells. As a result, the cell membrane bursts, but not the cell nucleus. Consequently, it is thus possible to extract the cytoplasm containing the RNA of the cell. After the extraction of the RNA, the DNA can be extracted in a second step, in which a hypertonic lysis buffer is drawn up. As a result, the cell nucleus also now bursts, and the DNA can be extracted. It is also possible to use only a hypertonic buffer, and the DNA and the RNA are extracted in one step.

Lysis buffers can differ in composition. A distinction must be made between hypotonic (lysis) buffer and hypertonic (lysis) buffer.

An exemplary composition of hypotonic lysis buffer contains a final concentration of 20 mM [millimol] Tris. This means that, in a mixture of sample and Tris, a final concentration of 20 mM NaCl is established.

An exemplary composition of hypertonic buffer contains 3% sodium chloride (NaCl). This means that, in a mixture of sample and NaCl, a final concentration of 3% NaCl is established.

After successful lysis, the RNA is converted into DNA by means of reverse transcription. This yields a solution consisting only of DNA. It can then be detected by means of quantitative real-time polymerase chain reaction (qPCR) for a detection reaction.

The actual core of the described method lies in the construct of the PCR system as indicated in FIG. 1 (steps g) and h)) and depicted in the following table:

| LEVEL | TRANSCRIPTOME | | | GENOME |
|---|---|---|---|---|
| Target | A | B | C | D |
| Cell type α | + | + | − | + |
| Cell type β | + | − | + | + |
| Material tested | mRNA | mRNA | mRNA | DNA |

The evaluation of the qPCR curves allows quantitative determination and makes it possible to infer the composition of the sample at the level of cell type.

The table describes the design strategy of the PCR system for the successful application of the described method. The basis of this is the detection of the composition of a cell suspension of a cell type or cell population α and another cell type or cell population β of a eukaryotic individual.

A specific example is detection of circulating tumor cells (type α) in a background of blood cells (type β). The basic strategy is to determine via the transcriptome (mRNA information) the cell types the relative cell pattern between the cell types. The measurement of the genome then makes it possible to determine the absolute count of all cells in the sample. If this count is known, it is then possible, together with the ratios, to estimate the absolute counts of cells having individual cell markers or the counts of the individual subpopulations (various types of cells within the sample).

The amount of all mRNA of a cell is referred to as the "transcriptome". It is a cell type-specific parameter.

Said transcriptome is the total amount of RNA available for classification in step d).

The sample or the first lysate of the sample comprising the total amount of RNA (transcriptome) is preferably checked stepwise for targets (i.e., for cell markers or cell types which are to be identified using the described method). Preferably, the individual targets are worked through in a certain order. For example, the targets to be tested are identified by the indices A, B, C and so on. The sample or the first lysate is first checked for target A, then for target B, then target C and so on. This is done in step d). If a certain gene is active in a cell, this corresponding DNA sequence is transcribed into RNA, which then migrates from the cell nucleus into the cytosome, where it is translated into a protein.

A cell type is identifiable on the basis of active and inactive genes. Every cell type has a defined group of genes which are particularly active or must be switched off. This gene activity can be shown by detection of the corresponding mRNA or proteins. RNA detections by qPCR are particularly sensitive here.

Instead of complete examination of the transcriptome and classification of all RNA in the transcriptome, what can also be detected by means of qPCR in step d) are only sequences typical of cell types. As already described, the mRNA is then transcribed into DNA for subsequent performance of a gene-specific qPCR. The transcription measurements make it possible to state the ratios of the transcription patterns of the cell(s). To this end, at least one target A is chosen which is expressed identically in all cell types, i.e., is active in the two types. This is a so-called housekeeping gene, which is generally constantly active across all cell types.

Typical examples thereof are GAPDH, actin, SDHA, HSP, COX8 or MYH9. As second target B, what is used is a target which is upregulated for cell type α, whereas the target is accordingly downregulated in cell type β. The third target C has a chiasmatic transcription profile in relation to target B, i.e., downregulated in cell type α and upregulated in cell type β.

The normalization via target A is necessary because cell populations are highly heterogeneous in their measurement parameters. Cell size in particular usually exhibits great variation. Small cells generally have lesser absolute numbers of mRNA, their ratios of up and downregulated, are conserved, however. Therefore, a housekeeping gene is used in order to normalize the size differences of the cells and to make them comparable. In the example of CTCs in blood, target B could thus be an epithelial marker such as EpCAM, CDK or catenin. As target C for blood cells (mainly leukocytes such as T cells, neutrophils, dendrites, macrophages), it is possible to use hematopoietic markers such as CD45.

Information as to how much sample material (i.e., what number of cells) was used is, now, measured via the genome. In this case, use is made of a target D which should be identical across all cell types of the individual to be measured. Especially genes with high SNP proportions or high mutation rates (e.g., oncogenes) are not suitable because such genes are present in different amounts precisely in various cells of the sample or because the amount of target cells (markers) is to be ascertained precisely on the basis of such genes using the described method. Ideally, highly conserved, multiple abundant genes such as an hLINE1 or APEX1 are used here. These are present multiple times and easier to quantify than a classic gene such as EGFR, which occurs exactly twice in the genome. Especially when few cells are available in a sample, such as in the case of customary CTC tests, this is advantageous.

The concept of the method described here is scalable as desired. In the transcriptome, it is possible to add a target E which serves for finer selection of the cell types, for statistical determination of quality or for introduction of additional cell types.

In connection with a liquid biopsy in the context of monitoring of tumor therapy, the described method can be carried out as follows. What can be measured in relation to the target B used, EpCAM, is, for example, additionally CDK19 or vimentin. Thus, an additional tumor cell marker. If the two expression patterns are too different, reaction problems can be inferred. The check as to whether the two expression patterns are identical can thus be used as a control element for the validity and quality of the sample material. In addition, the additional target E can be used for the introduction of a third cell type $\gamma$. In the context of CTC monitoring, the additional target E presents itself as a marker of mesenchymal tumor cells, such as, for example, Twist, N-Notch, vimentin or Snail1. Therefore, the population of CTCs can be divided again into two subtypes. Therefore, the method can also be used in the context of examinations in the area of epithelial-to-mesenchymal transition (EMT). This is of particular interest because an EpCAM bias is therefore avoided, since a considerable portion of mesenchymal cells are also present in blood.

Figure 2:
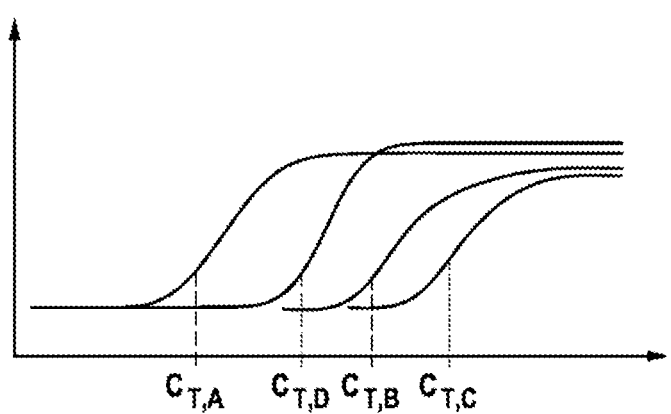
FIG. 2: shows, by way of example, parameters for classifying RNA under cell markers.

FIG. 2 shows the analysis chain of the method described in the table above. What are determined here from the qPCR curves of the individual components A, B, C, D are the respective CT value threshold cycles. For the transcription elements, the relative expression patterns are then determined via the standard $\Delta\Delta CT$ method. This makes it possible to ascertain the expression ratios of the individual cell types. The absolute number of cells in the reaction mixture is determined from the genetic material.

Figure 3:
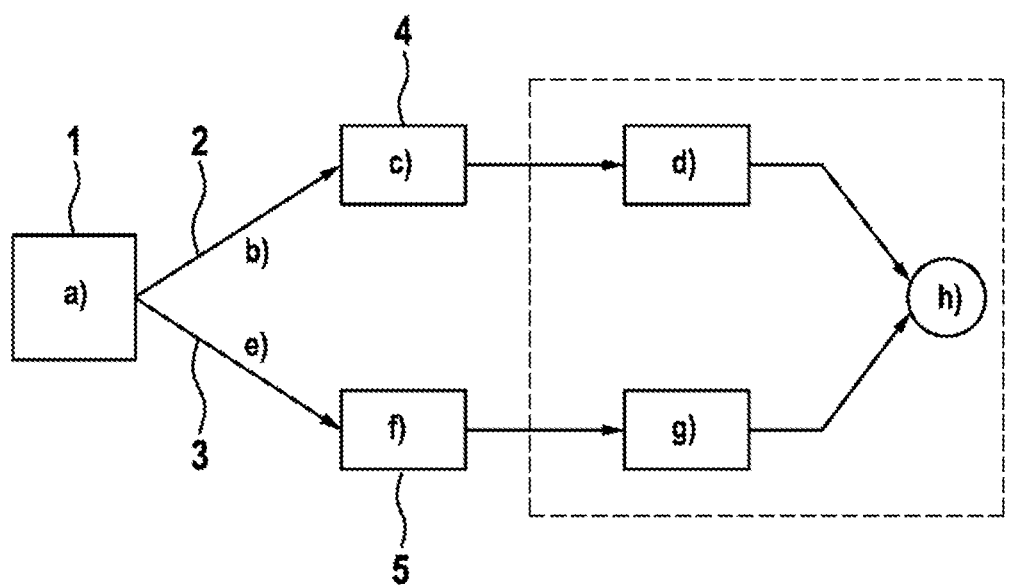
FIG. 3: shows a further flow chart of the described method

FIG. 3 shows an alternative schematic depiction of the process management of the described method. Instead of the measurement of the targets in one reaction mix, the transcriptome can be separated from the DNA in a first step. This involves using selective lysis methods in which initially only the cytosol containing mRNA is lysed by means of a hypertonic buffer (lysis buffer), followed by the lysis of the DNA-containing cell nucleus via a hypotonic lysis buffer. The depiction in FIG. 3 shows that steps b), c) and d) concerning the isolation and evaluation of the RNA are in principle considered to be separate from steps e), f) and g) concerning the isolation and evaluation of the DNA. Process step d) and process step g) both provide information which form the basis of the performance of process step h) and are therefore made available to process step h).

The invention claimed is:

1. A method for the detection of certain characteristic cells in a sample, comprising:
   providing a sample of cell suspension;
   performing a first lysis operation with the sample to yield a first lysate of the sample, wherein the first lysis is done such that cell nuclei of the cells of the sample remain intact;
   extracting ribonucleic acids (RNA) freely available in the first lysate;
   classifying the extracted RNA to ascertain the amounts of various types of RNA in the first lysate;
   performing a second lysis operation with the sample on which the first lysis was performed to yield a second lysate of the sample, wherein the second lysis is done such that the cell nuclei of the cells in the sample are destroyed;
   extracting deoxyribonucleic acids (DNA) freely available in the second lysate;
   calculating a total cell count of cells in the provided sample on the basis of the amount of extracted deoxyribonucleic acids; and
   calculating numbers of cells having individual cell markers in the provided sample on the basis of the ascertained amounts of various types of ribonucleic acids and the calculated total cell count.

2. The method as claimed in claim 1, further comprising:
   identifying CTCs (circulating tumor cells) on the basis of the individual cell markers.

3. The method as claimed in claim 1, wherein the individual cell markers comprise at least one of the following markers:
   epithelial marker;
   EpCAM;
   CD45; and
   cytokeratin.

4. The method as claimed in claim 1, wherein calculating numbers of cells having individual cell markers comprises:
   preparing a hemogram.

5. The method as claimed in claim 1, wherein variation in the cell sizes of the cells in the sample is taken into account in at least one of calculating the total cell count of cells in the provided sample and calculating numbers of cells having individual cell markers in the provided sample.

6. The method as claimed in claim 1, further comprising:
   distinguishing active RNA and inactive RNA prior to calculating numbers of cells having individual cell markers in the provided sample.

7. The method as claimed in claim 3, wherein calculating the total cell count of cells in the provided sample is done by a comparison of the ascertained amounts of various types of RNA in the first lysate with a data matrix in which data concerning RNA present are stored for each individual cell marker.

8. The method as claimed in claim 1, further comprising:
   extracting cytoplasm prior to extracting the RNA freely available in the first lysate.

9. The method as claimed in claim 1, wherein classifying the extracted RNA comprises:
   converting the RNA into DNA to ascertain the amounts of various types of RNA in the first lysate.

10. The method as claimed in claim 1, wherein performing the first lysis comprises changing an osmotic equilibrium in the sample, thereby bringing about bursting of the cell membranes of the cells.

11. The method as claimed in claim 10, wherein an osmotic equilibrium is set in performing the first lysis such that cell nuclei of cells in the sample remain intact.

* * * * *